(12) United States Patent
Dekker

(10) Patent No.: US 6,709,402 B2
(45) Date of Patent: Mar. 23, 2004

(54) APPARATUS AND METHOD FOR MONITORING RESPIRATION WITH A PULSE OXIMETER

(75) Inventor: Andreas Lubbertus Aloysius Johannes Dekker, Maastricht (NL)

(73) Assignee: Datex-Ohmeda, Inc., Madison, WI (US)

( * ) Notice: Subject to any disclaimer, the term of this patent is extended or adjusted under 35 U.S.C. 154(b) by 2 days.

(21) Appl. No.: 10/081,168

(22) Filed: Feb. 22, 2002

(65) Prior Publication Data

US 2003/0163033 A1 Aug. 28, 2003

(51) Int. Cl.⁷ ................................. A61B 5/08
(52) U.S. Cl. ....................... 600/529; 600/324
(58) Field of Search .............. 600/310, 322, 600/323, 324, 325, 330, 336, 529

(56) References Cited

U.S. PATENT DOCUMENTS

| | | |
|---|---|---|
| 3,704,706 A | 12/1972 | Herczfeld et al. |
| 4,306,567 A | 12/1981 | Krasner |
| 4,379,460 A | 4/1983 | Judell |
| 4,404,974 A | 9/1983 | Titus |
| 4,510,944 A | 4/1985 | Porges |
| 4,765,340 A | 8/1988 | Sakai et al. |
| 4,777,960 A | 10/1988 | Berger et al. |
| 4,781,201 A | 11/1988 | Wright et al. |
| 4,813,427 A | 3/1989 | Schlaefke et al. |
| 4,858,638 A | 8/1989 | Cseri ........................ 137/115 |
| 4,860,759 A | 8/1989 | Kahn et al. |
| 4,863,265 A | 9/1989 | Flower et al. |
| 4,869,254 A | 9/1989 | Stone et al. |
| 4,884,578 A | 12/1989 | Morgenstern |
| 4,899,760 A | 2/1990 | Jaeb et al. |
| 4,930,517 A | 6/1990 | Cohen et al. |
| 4,958,638 A | 9/1990 | Sharpe et al. |
| 4,960,129 A | 10/1990 | dePaola et al. |
| 4,972,842 A | 11/1990 | Korten et al. |
| 5,033,472 A | 7/1991 | Sato et al. |
| 5,078,136 A | 1/1992 | Stone et al. |
| 5,101,825 A * | 4/1992 | Gravenstein et al. ........ 300/326 |
| 5,111,817 A | 5/1992 | Clark et al. |
| 5,170,794 A | 12/1992 | Reiche |
| 5,273,036 A * | 12/1993 | Kronberg et al. ............ 600/310 |
| 5,368,224 A | 11/1994 | Richardson et al. |
| 5,385,144 A * | 1/1995 | Yamanishi et al. |
| 5,396,893 A | 3/1995 | Oberg et al. |
| 5,398,682 A * | 3/1995 | Lynn ........................... 600/335 |

(List continued on next page.)

FOREIGN PATENT DOCUMENTS

WO    WO 01/76471 A1 * 10/2001

OTHER PUBLICATIONS

Spectral Analysis: Review "Heart Rate Variability", Lukas Spieker, hemodynamics.ucdavis.edu, Unknown Publication Date.

*Primary Examiner*—Eric F. Winakur
(74) *Attorney, Agent, or Firm*—Marsh Fischmann & Breyfogle LLP

(57) ABSTRACT

An apparatus and method for monitoring a secondary physiological process through variations caused by the secondary process in an optical signal used to calculate values related to blood oxygen levels. In particular, the optical signal may be divided into distinct portions such that a portion more directly affected by a particular secondary physiological process may be isolated and the secondary physiological process monitored. The apparatus and method is particularly useful for photoplethysmographically monitoring a patient's respiration frequency through changes in relative concentrations of blood oxygen related values that are proportionally related to the amounts of venous and arterial blood in a portion of tissue.

22 Claims, 4 Drawing Sheets

U.S. PATENT DOCUMENTS

| | | |
|---|---|---|
| 5,423,322 A | 6/1995 | Clark et al. |
| 5,431,159 A | 7/1995 | Baker et al. |
| 5,482,036 A | 1/1996 | Diab et al. |
| 5,490,505 A | 2/1996 | Diab et al. |
| 5,511,553 A | 4/1996 | Segalowitz |
| 5,553,615 A | 9/1996 | Carim et al. |
| 5,555,882 A | 9/1996 | Richardson et al. |
| 5,575,284 A | 11/1996 | Athan et al. |
| 5,623,933 A | 4/1997 | Amano et al. |
| 5,755,229 A | 5/1998 | Amano et al. |
| 5,766,127 A | 6/1998 | Pologe et al. ............... 600/310 |
| 5,776,071 A | 7/1998 | Inukai et al. ............... 600/493 |
| 5,830,137 A | 11/1998 | Scharf ........................ 600/323 |
| 5,842,979 A | 12/1998 | Jarman ....................... 600/322 |
| 5,853,364 A | 12/1998 | Baker, Jr. et al. ........... 600/300 |
| 5,862,805 A | 1/1999 | Nitzan ....................... 128/898 |
| 5,865,167 A | 2/1999 | Godik |
| 5,865,756 A | 2/1999 | Peel, III ..................... 600/490 |
| 5,885,213 A | 3/1999 | Richardson et al. ........ 600/336 |
| 5,902,235 A | 5/1999 | Lewis et al. ................ 600/323 |
| 5,919,134 A | 7/1999 | Diab .......................... 600/323 |
| 5,931,779 A | 8/1999 | Arakaki et al. ............. 600/310 |
| 5,934,277 A | 8/1999 | Mortz |
| 5,954,644 A | 9/1999 | Dettling et al. ............. 600/322 |
| 5,971,930 A | 10/1999 | Elghazzawi ................. 600/483 |
| 5,980,463 A | 11/1999 | Brockway et al. .......... 600/485 |
| 5,993,893 A | 11/1999 | Kikuchi ........................ 427/8 |
| 5,997,482 A | 12/1999 | Vaschillo et al. ........... 600/484 |
| 6,011,985 A | 1/2000 | Athan et al. ................ 600/322 |
| 6,027,455 A | 2/2000 | Inukai et al. ............... 600/490 |
| 6,028,311 A | 2/2000 | Sodickson et al. .......... 250/343 |
| 6,064,910 A | 5/2000 | Andersson et al. ........... 607/20 |
| 6,067,462 A | 5/2000 | Diab et al. .................. 600/310 |
| 6,081,742 A | 6/2000 | Amano et al. .............. 600/513 |
| 6,099,481 A | 8/2000 | Daniels et al. .............. 600/538 |
| 6,129,675 A | 10/2000 | Jay ............................. 600/485 |
| 6,155,992 A | 12/2000 | Henning et al. ............. 600/583 |
| 6,480,733 B1 | 11/2002 | Turcott ....................... 600/516 |
| 6,529,752 B2 * | 3/2003 | Krausman et al. .......... 600/323 |

\* cited by examiner

APPARATUS AND METHOD FOR MONITORING RESPIRATION WITH A PULSE OXIMETER

FIELD OF THE INVENTION

The present invention relates generally to medical diagnostic instruments and, more specifically, to the field of photoplethysmography and using a plethysmographic system to monitor secondary physiological processes based on a plethysmographic signal.

BACKGROUND OF THE INVENTION

During many medical procedures, especially surgical procedures, it is desirable to monitor the functioning of a patient's cardiopulmonary system (i.e., the heart and lungs) to determine a patient's current condition. Various methods for measuring physiological functioning of the cardiopulmonary system exist. Lung functioning may be monitored through the frequency of a patient's respiration using, for example, respiration sensors based on thermistors placed in the respiratory path in front of the mouth and/or nose or breathing belts applied around the chest and abdomen for mechanical pulmonary monitoring. Additionally, a patient's heart may also be monitored during a given procedure. Again, numerous methods exist for monitoring a patient's heart rate from manually checking with a stethoscope to the use of pressure transducers applied to the skin. A disadvantage of such cardiopulmonary measurement methods is that a measurable respiratory movement and/or heart rate is by no means a sign of effective cardiopulmonary operation. For example, in cases where there are obstructions in the respiratory pathway or uncoordinated, out of phase chest and abdominal respiration, a patient may be breathing and their heart may be beating, but oxygen is not being efficiently transferred to their bloodstream. Therefore, it is often desirable to monitor a patient's blood oxygen saturation levels to assure that effective cardiopulmonary functioning is occurring.

Blood oxygen saturation ($SpO_2$) levels of a patient's arterial blood may be monitored using a pulse oximeter, which typically measures the absorption of red and infra red light applied to a patient's tissue by oxygenated hemoglobin and deoxygenated hemoglobin in the blood. Pulse oximeters commonly comprise a sensor that is releaseably attached to a patient's appendage, such as a finger, ear lobe or nasal septum, for a given medical procedure. The sensor typically includes a detector and at least one red light source and one infrared light source that may be focused on or through a patient's tissue. The detector detects the light that reflects from or passes through the patient's tissue. This light detector, typically a photodetector, produces what is termed a "plethysmographic signal" indicative of the light attenuation caused by the absorption, reflection and/or diffusion due to the tissue on which the light is directed. This measured absorption data from the plethysmographic signal allows for the determination of the relative concentration of de-oxyhemoglobin (RHb) and oxyhemoglobin ($HbO_2$) and, therefore, ($SpO_2$) levels, since de-oxyhemoglobin absorbs more light than oxyhemoglobin in the red band and oxyhemoglobin absorbs more light than de-oxyhemoglobin in the infrared band, and since the absorption relationship of the two analytes in the red and infrared bands are known. See, for example, U.S. Pat. Nos. 5,934,277 and 5,842,979.

As may be appreciated, in order to accurately monitor a patient's cardiopulmonary functioning, it is often necessary to use a combination of three separate monitors, a pulse oximeter, a respiratory monitor and a heart rate monitor.

SUMMARY OF THE INVENTION

A primary objective of the present invention is to use plethysmographic signals to monitor a secondary physiological process of the patient such as respiration or heart rate.

A related objective is to use optical signals to monitor a patient's respiration rate.

A further related objective is using multi-channel optical signals transmitted through a patient's tissue to monitor respiration rate.

Another objective is using plethysmographic signals obtained during a given time period to monitor both blood oxygenation and respiration rate.

A further objective of the present invention is to provide a practical algorithm for monitoring variations in a blood analyte composition that are indicative of a patient's respiration.

In accordance with the above objectives, the inventor has recognized that the signals produced by various monitoring devices for monitoring physiological processes of the human body typically include minor variations which are indicative of a secondary physiological processes. In particular, the inventor has recognized that plethysmographic signals contain two components of interest which each may contain minor variations indicative of secondary processes occurring in and/or affecting the cardiopulmonary system. The first component of interest is a low frequency or substantially invariant component in relation to the time increments considered for blood oxygen saturation calculations, sometimes termed the "DC component," which generally corresponds to the attenuation related to the non-pulsatile volume of the perfused tissue and other matter that affects the transmitted plethysmographic signal. The second component sometimes termed the "AC component," generally corresponds to the change in attenuation due to the pulsation of the blood. In general, the AC component represents a varying wave form which corresponds in frequency to that of the heartbeat. In contrast, the DC component is a more steady baseline component, since the effective volume of the tissue under investigation varies little or at a low frequency if the variations caused by the pulsation of the heart are excluded from consideration. However, the inventor has recognized that the DC component does vary over a low frequency and small amplitude and that this variation in the DC component is generally attributable to changes in the monitored tissue caused by spill-over effects of various physiological processes of the body including cardiopulmonary processes. Finally, the inventor has recognized that by determining what causes a particular variation in the DC component of the plethysmographic signal it may be possible to monitor a secondary physiological process such as respiration in addition to blood oxygen levels while using a pulse oximeter. Additionally, the inventor has realized the advantages of being able to supply additional physiological information regarding a patient's health during a medical procedure while reducing the number of monitors attached to the patient.

One or more of the above objectives and additional advantages are indeed realized by the present invention where, in one aspect, an apparatus is disclosed to monitor at least one secondary physiological process through variations caused by that physiological process in at least a portion of an optical signal used to calculate a value related to blood oxygenation levels. The apparatus comprises one or more emitters for controllably emitting at least first and second wavelengths of electromagnetic radiation onto or through a portion of living tissue and a detector for detecting signals relative to the transmitted first and second wavelengths of electromagnetic radiation passing through or being reflected from the tissue. The detector is further operable to produce at least a first detector output signal indicative of the electromagnetic radiation passing through or reflected from the tissue. The apparatus also includes a processor which is operative to produce a first output value related to blood oxygen levels of the tissue through a mathematical computation using at least a portion of the detector signal corresponding to each wavelength of electromagnetic radiation applied to the tissue. Further, the processor is able to monitor this first output related to the tissue's blood oxygen levels over a predetermined period to identify variations therein that are indicative of a secondary physiological process. Finally, the processor generates a second output signal indicative of the secondary physiological process.

As will be appreciated, numerous physiological processes of the human body are interrelated. In particular, the different physiological systems of the body are often interrelated such that a process in a first system may have a measurable spill-over effect on a second system. These systems may include, but are not limited to, the respiratory system, the circulatory system, the central nervous system, the vasomotor system, etc. For example, where a first physiological process is related to the cardiovascular system, such as blood pressure or pulse, it is common for there to be measurable spillover effects (e.g., changes in blood pressure) in this process caused by respiratory system processes such as inspiration and expiration. Thus, by measuring spillover effects caused by a second physiological process in a monitored first physiological process, a second physiological process may be simultaneously monitored.

With regard to the apparatus' first emitter, a light emitting diode (LED) may be used to produce first and second wavelengths of electromagnetic radiation, or a separate LED may be used for each separate wavelength of electromagnetic radiation to be transmitted to the patient's tissue. For example, a first LED may be used to emit electromagnetic radiation in the visible spectrum and a second LED may be used to emit electromagnetic radiation in the infrared range. However, it will be appreciated that the first and second wavelengths of electromagnetic radiation may both be in or outside of the visible spectrum so long as the wavelengths are of sufficiently different frequencies such that absorption rates of the tissue may be calculated.

The electromagnetic radiation applied to the tissue may pass through the tissue to which it is applied, be reflected back from the tissue, or in any suitable way interact with the tissue such that the tissue modulates the signals received by one or more detectors. These detectors will generally comprise one or more photodetectors which receive the electromagnetic radiation as an analog signal having both an AC and DC component. The photodetector is operative to produce an output signal indicative of this electromagnetic radiation for receipt by a processor. The output signal may be a single multiplexed signal or a separate signal for each wavelength of electromagnetic radiation applied to the tissue. Generally the detector signal will reflect the AC and DC components of the received analog signals. As will be appreciated, the LED(s) and the photodetector(s) may be incorporated into a single plethysmographic sensor which may, for example, be attachable to a patient's appendage such as a finger, ear lobe, nasal septum, etc., or the sensor may attach to a body part such as a thigh, abdomen, etc. and emit light into the tissue and then detect a portion of the original signal reflected back by the tissue.

The processor of the inventive apparatus is operative to receive the output signal(s) from the detector and use this signal(s) to determine at least one value related to circulatory parameters. For example, by using a component of the detector signal, the processor may be configured to monitor a predetermined frequency range and determine a patient's pulse rate though variations in the amplitude of the signal. In addition, by mathematically processing a first and second portion of the detector signal corresponding to a portion of each wavelength of electromagnetic radiation applied to the tissue, a blood oxygen saturation level ($SpO_2$) may be determined using, for example, a look-up tables or appropriate algorithms. The processor may be further operative to monitor this first value for variations such as periodic increases or decreases which are caused by a secondary cardiopulmonary process. Furthermore, the processor may be operative to monitor these variations in a predetermined frequency range, which may help isolate a particular secondary physiological process. For example, for respiration where it can be expected that an adult patient will respire between 0 and 30 times per minute a frequency range of 0 to 0.5 hertz may be monitored whereas for a newborn that may respire 60 times or more per minute a frequency range of 0 to 1.5 hertz may be monitored. Alternatively, the processor may be configured such that it is able to isolate (e.g., filter) and individually use either the AC component or the DC component of the detector signal to perform the above said functions such that a particular physiological process may be better isolated.

In another aspect of the current invention, a method is provided to monitor at least one secondary physiological process through variations caused by that process in at least a portion of an optical signal used to calculate a value related to blood oxygenation levels. The method comprises the steps of applying electromagnetic radiation of one or more known wavelengths to a portion of tissue, detecting the intensity of the electromagnetic radiation relative to that portion of tissue, generating at least a first signal indicative of the detected radiation, processing this signal(s) such that at least a first value related to blood oxygen levels is produced, and monitoring this first value over a predetermined time to identify variations indicative of a secondary physiological process. Finally, the method includes generating an output signal indicative of the secondary physiological process.

The step of applying electromagnetic radiation may further comprise controllably alternating one or more light sources such that when a first light source is activated and applied to the tissue, a second light source is deactivated and has no effect on the tissue. Alternatively, the light sources may be applied to the tissue simultaneously such that a non-time division multiplexed signal will result at the detector. Additionally, the electromagnetic radiation may be applied to the tissue in one or more ways. For example, the electromagnetic radiation may be applied such that it travels through a portion of the tissue (e.g., through a fingertip, ear lobe, nasal septum, etc.) or the electromagnetic radiation may be applied such that a portion of it is reflected from the tissue. Accordingly, the step of detecting the electromagnetic radiation may comprise receiving a portion of the applied electromagnetic radiation after it passes through a portion of the tissue or receiving a portion of the applied electromagnetic radiation reflected from the tissue.

The step of processing may comprise using a portion of the detected signal(s) for producing a first value related to blood oxygen levels. In particular, the detected signal(s) may be filtered to isolate discrete portions of the signal. Once the signals are filtered, values may be monitored in each of the discrete signal portions such that a first blood oxygen related value may be determined. Once a first value is determined, it may be monitored for variations known to be associated with a secondary process such as a cardiopulmonary process. For example, in the case where the first value is a patient's $HbO_2$/Hb ratio, an increase in the ratio over a known time period may be indicative of respiration. As will be appreciated, if a variation caused by respiration is identified in the ratio an output may be generated indicative of respiration.

In another aspect of the present invention, an apparatus is provided for monitoring respiration using optical signals to identify changes caused by the respiration in values related to blood oxygen levels. The apparatus comprises an emitter for emitting first and second wavelengths of the electromagnetic radiation to a portion of living tissue, a detector for detecting the first and second wavelengths of electromagnetic radiation as applied to the tissue and for producing a detector signal indicative thereof, and a processor. The processor is operative for filtering the detector signal such that individual portions of the detector signal may be isolated. The processor is configured to determine a value related to blood oxygen levels in the monitored tissue through mathematical computation using at least a first portion of each filtered signal. Once the blood oxygen related value is determined for the tissue, it may be intermittently, periodically or substantially continuously monitored to determine increases and decreases which are indicative of the patient's respiration. Finally, upon determining changes in the blood value indicative of respiration, the processor may generate an output signal showing a patient's respiration frequency.

The apparatus may contain a number of electromagnetic radiation emitting devices for emitting radiation to the portion of living tissue. Again, these may comprise light emitting diodes (LEDs) which may emit electromagnetic radiation in the visible light range and/or the near infrared range. The radiation emitted by these emitters will generally be detected by a photodetector capable of detecting radiation in the applied wavelengths and further capable of producing an output signal indicative of the electromagnetic radiation passing through or reflected from the tissue for each wavelength. The electromagnetic radiation passing through or reflecting from the tissue will generally comprise an AC and a DC component. Therefore, the signal produced by the detector will contain an AC and a DC component.

Once the detector produces the detector output signals, they may be received by the processor and its filtering module such that one or more portions of each signal may be isolated. For example, if the detection signals contain both an AC and DC component, the filtering module may be operable to remove and/or isolate either the AC or DC component. Additionally, the filter may comprise a band-pass filter which is capable of isolating portions of the detected signals according to frequency. As will be appreciated, the AC component is typically a higher frequency component than the DC component, therefore a high-pass filter may be used to remove the AC component from the detected signal.

The processor is further configured to determine blood analyte values related to the blood oxygen levels of the monitored tissue through a mathematical computation using at least a first portion of the first filtered signal and a first portion of the second filtered signal. For example, the processor may be configured such that it is able to determine values related to the Ratio of Ratios that is conventionally used in determining oxygen saturation levels. As will be appreciated, by using the filtered signals which may only contain a DC or AC component, the oxygen saturation level determined will be related only to that component. For example, the DC component of the detected electromagnetic signal represents the detected portion of the electromagnetic radiation as applied to the tissue as a whole where the AC portion represents the variation in volume in that portion of tissue due to variation in blood volume caused by the pulse. Therefore, by using the DC signal, the blood analyte values in the tissue independent of the pulsatile AC component may be determined.

Once the blood oxygen analyte related values are determined for the desired component (e.g., AC or DC) of the detected signals, this value may be monitored for increases and decreases indicative of respiration. For example, increases in blood oxygen levels over a predetermined frequency range may be correlated with known physiological effects caused by respiration. More particularly, increases in the ratio of oxygenated hemoglobin over deoxygenated hemoglobin over a frequency of 0 to 0.5 hertz may be caused due to inspiration (breathing in), which has the effect of lowering the amount of venous blood in the tissue and thus increases the ratio of arterial (oxygenated) blood to deoxygenated blood in the tissue.

DETAILED DESCRIPTION

The present invention relates to monitoring a secondary cardiopulmonary process of the body through spillover effects reflected in one or more signals analyzed with respect to monitoring a first physiological parameter. More particularly, the invention relates to monitoring a patient's respiration through variations caused thereby in a plethysmographic signal used for monitoring blood analyte concentrations related to blood oxygen saturation levels.

A pulse oximeter generally determines the saturation value of blood by analyzing values related to the time-varying signal attenuation characteristics of the blood. When radiant energy passes through a liquid, certain wavelengths may be selectively attenuated by the liquid. For a given path length that the light traverses through the liquid, Beer's Law (the Beer-Lambert relation) indicates that a relative reduction in radiation power at a given wavelength is the inverse logarithmic function of the concentration of the components in the liquid that absorb that wavelength.

In general, pulse oximetry utilizes the relative difference between the electromagnetic radiation attenuation of de-oxyhemoglobin, RHb, and that of oxyhemoglobin, $HbO_2$. The electromagnetic radiation attenuation of RHb and $HbO_2$ are characteristically tied to the wavelength of the electromagnetic radiation traveling through them. As known by those skilled in the art, de-oxyhemoglobin molecules absorb more red light than oxyhemoglobin molecules and the absorption of infrared electromagnetic radiation is substantially unaffected by the presence of oxygen in the hemoglobin molecules. Thus, both RHb and $HbO_2$ absorb electromagnetic radiation having a wavelength in the infrared (IR) region to approximately the same degree; however, in the visible region, the light absorption coefficient for RHb is quite different from the light absorption coefficient of $HbO_2$ because the $HbO_2$ absorbs significantly more light in the visible spectrum than RHb.

In the practice of pulse oximetry, the oxygen saturation of hemoglobin in the blood is determined by illuminating a volume of intravascular blood with electromagnetic radiation of two or more selected wavelengths, detecting the time-varying electromagnetic radiation intensity transmitted through or reflected by the intravascular blood, and calculating oxygen saturation values for a patient's blood by applying the Lambert-Beer transmittent law to the detected transmitted or reflected electromagnetic radiation intensity at the selected wavelength.

Figure 1:
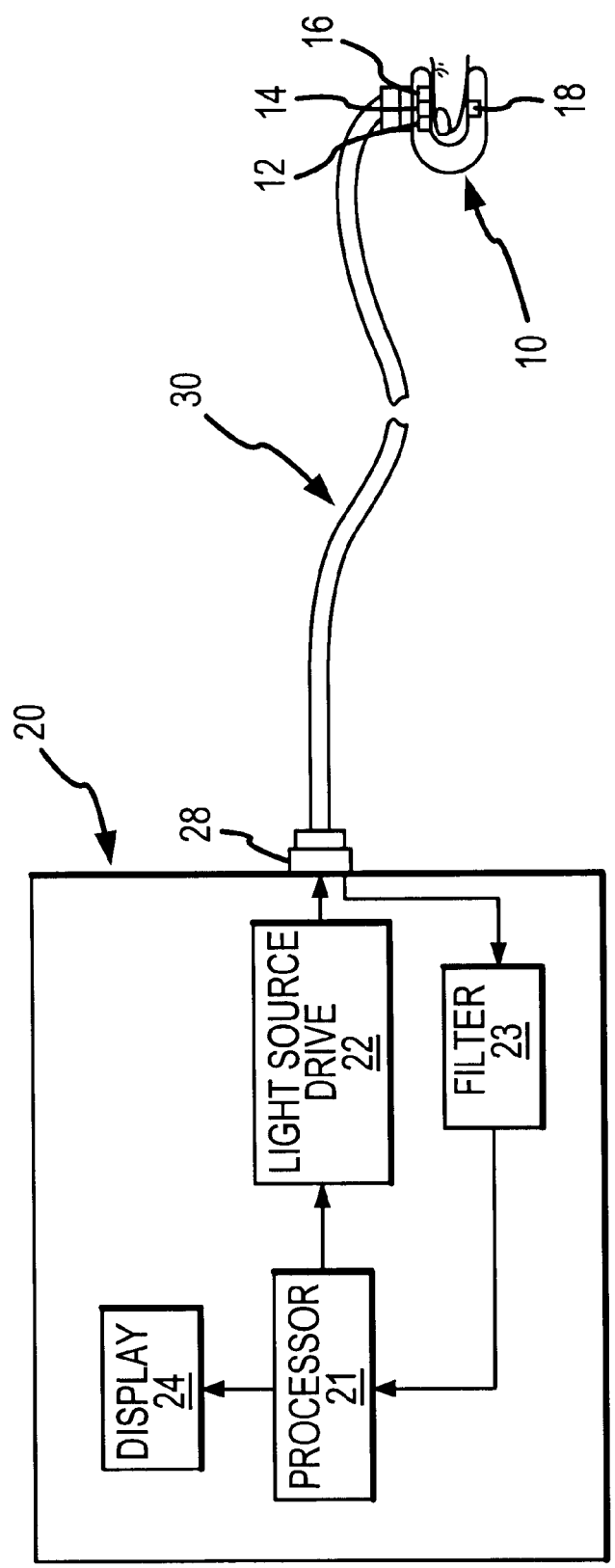
FIG. 1 is a schematic representation of a photoplethysmographic system in accordance with the present invention.

FIG. 1 generally illustrates a pulse oximetry system in which the present system is implemented. In the application of FIG. 1, a plethysmographic sensor 10 is interconnected to a plethysmographic monitor 20 by a cable 30. In operation of the system, the plethysmographic monitor 20 may comprise a processor 21 that triggers light source drivers 22 to transmit drive signals via cable 30 to light sources 12, 14 and/or 16 comprising sensor 10. In turn, light sources 12, 14 and/or 16 emit light signals at different corresponding centered wavelengths. By way of example, in the system application shown in FIG. 1, light sources 12 and 14 may illuminate a patient's tissue such as a fingertip under test. Upon tissue illumination, a photodetector 18 comprising sensor 10 may detect the intensity of light transmitted through the tissue under test and provide a corresponding output signal. Generally, in photoplethysmographic measurements, light sources 12, 14 and/or 16 will comprise light emitting diodes (LEDs) with at least a first LED emitting light in a frequency in the infrared range and at least a second LED emitting light in the red range of the visible light spectrum. It will be appreciated that the sources 12, 14 and 16 and/or the detector may be located in the monitor 20 or within the cable 30 rather than in the sensor 10 as illustrated.

The signal produced by the photodetector 18, typically a multiplexed analog signal, includes portions indicative of the intensity of the red and infrared electromagnetic radiation that passed through or was reflected from the tissue. These portions may be segregated using sampling devices, such as a filter 23 or demodulating modules, which may be embodied in hardware or software, so as to provide separate signals representing the red and infrared light transmission of the body's structure, as will be more fully discussed below. Additionally, the electromagnetic radiation or 'light' received by photodetector 18 comprises an analog signal that includes both an AC and a DC component for each wavelength of light emitted through the tissue. The AC component of the received signal reflects the varying optical absorption by the blood due to the variances in the volume of the blood present in the tissue. As will be appreciated this variance is caused by the pulsatile flow of the blood in the body due to the beating of the heart. When the heart beats, the volume of blood in a patient's arteries and veins increases slightly, increasing the total volume of blood and tissue through which the emitted light must pass. This increase in blood volume causes more of the emitted light signal to be absorbed and thus decreases the intensity or amplitude of the signal passing through the tissue.

Additionally, the properties of arterial and venous blood in the tissue vary in relation to the pulse cycle. The signal received by the photodetector also includes a DC component related to light absorption of the tissue, bone, venous blood, capillary blood and no-pulsatile arterial blood (hereinafter tissue). As will be appreciated, this tissue volume is considerably larger than the varying volume of arterial blood contained therein, therefore, the DC component of the attenuation signal is considerably larger than the AC component. Additionally, since the volume of the tissue in absence of the pulsatile flow remains fairly constant the DC component is often termed an invariant component. However, the volume of this tissue, and therefore the DC component of the signal does vary slightly over a low frequency. This variance is caused by one or more physiological processes independent of the pulsatile flow, as will be discussed more fully herein. The oximeter may include a number of additional components not illustrated including amplifiers, an analog-to-digital converter and other components for conditioning the signal.

Figure 2:
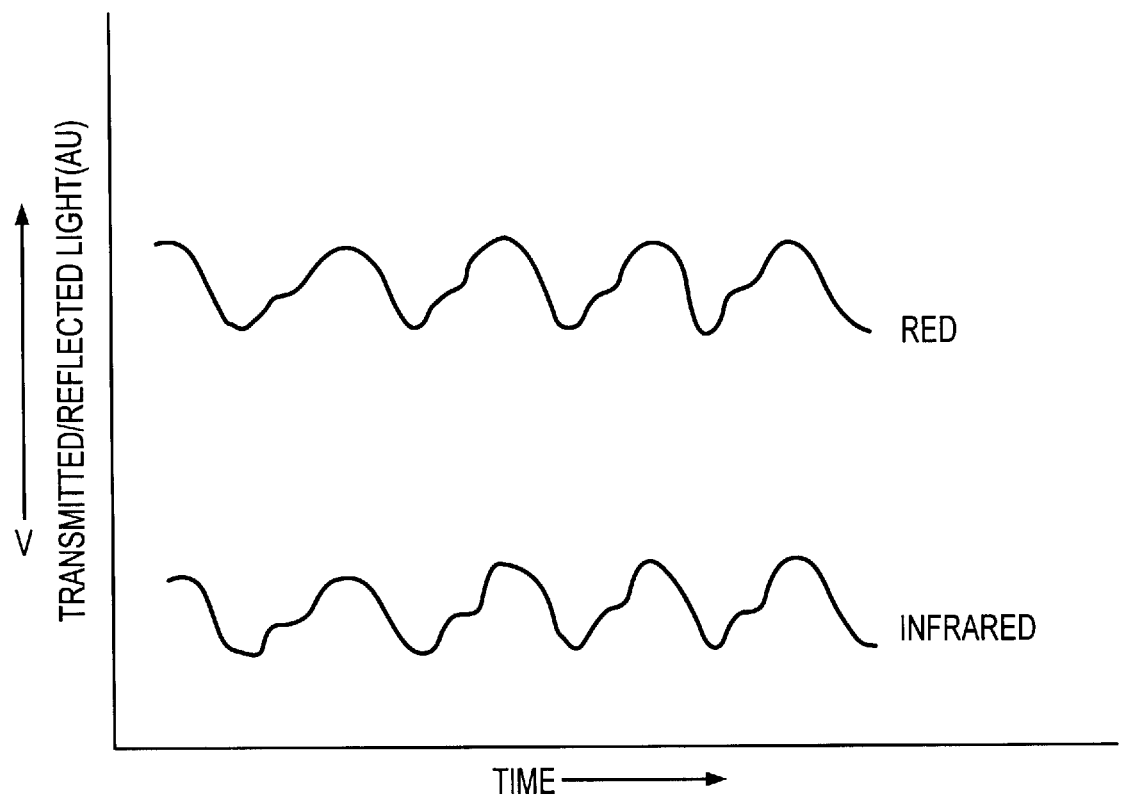
FIG. 2 shows an exemplary 'raw' photoplethysmographic waveform for a red and infrared channel.

FIG. 2 illustrates a red and infrared waveform representing the signals received by photodetector 18. These waveforms, called plethysmographic waves have a pulsatile nature and represent a 'raw' plethysmographic signal which show the intensity or absorption of the light passing through the tissue over time. In order for the monitor 20 to produce these waveforms for the display 24, the analog signals received by the photodetector 18 have to be converted to digital signals. This is accomplished using an analog to digital (A/D) converter, which produces a digital representation of the analog signals. This A/D converter 28 is operatively disposed between the detector 18 and the processor 21. The pulses in each of the signals represent the rising and falling intensity or attenuation of the light transmitted through or reflected by the tissue caused by the beating of the heart. Each time the heart pulses, the amount of blood in the tissue increases, increasing the amount of light absorbed therein and causing a lowered intensity reading in the plethysmographic signals. As the blood vessels relax between heartbeats, the amount of blood in the tissue is reduced and less light is absorbed. It should be noted that since the red and infrared light pass through substantially the same tissue the photoplethysmographic waveforms for the red channel will be shaped nearly identical to those in the infrared channel, only the amplitude of the red and infrared signal will significantly differ. Additionally, as shown in FIG. 2, the plethysmographic wave for each the red and infrared wavelength is a combination of the AC and DC component and that, as shown, a large base portion of the DC component has been removed such that the amplitude changes of the plethysmographic signal may be better shown. These changes in amplitude correspond with the pulse rate of the patient, which may be readily determined from this raw plethysmographic signal. The AC and DC components of each of the plethysmographic waves may be separated (i.e., filtered) from one another such that these components may be individually monitored.

Figure 3:
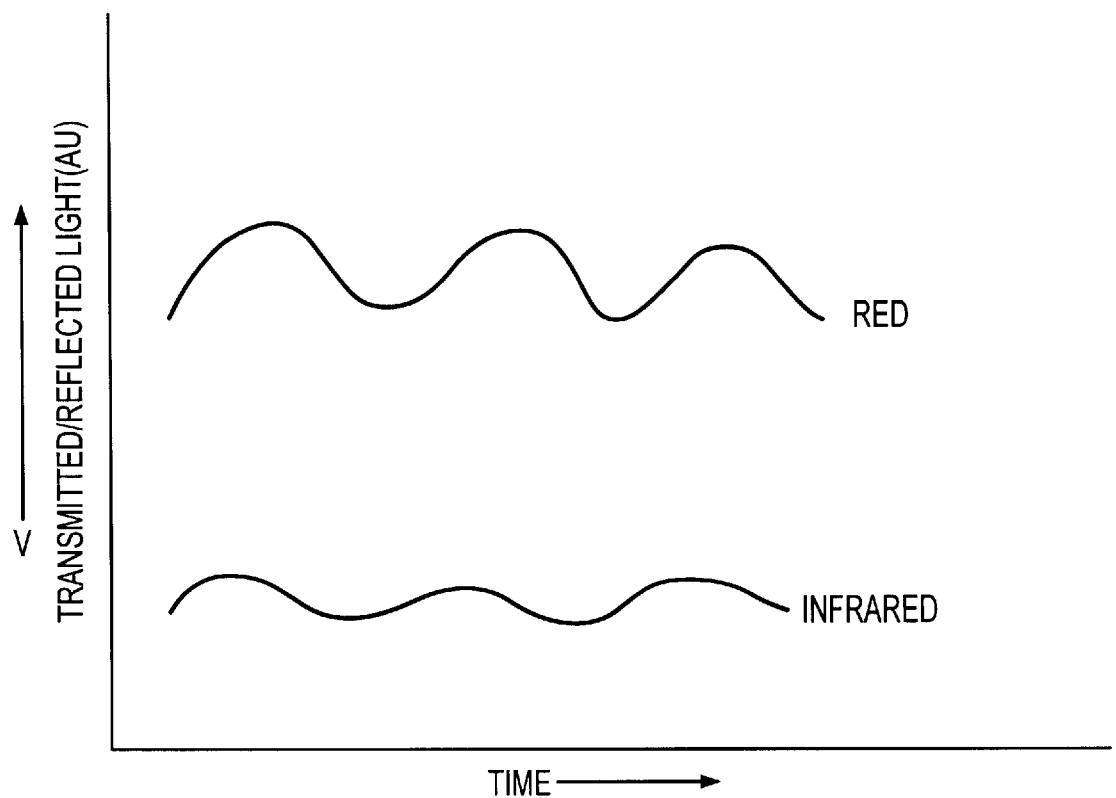
FIG. 3 shows a filtered DC component of a photoplethysmographic waveform for a red and infrared channel.

FIG. 3 shows an infrared and red plethysmographic wave in which the AC component has been filtered off, leaving the DC baseline signal. As shown in FIG. 3, the amplitude of the DC signal varies slightly over time even with the pulsatile AC component removed from the plethysmographic signal. This slow change in amplitude is caused by gradual changes in the thickness of the measured tissue (for example, a fingertip), which causes a variance in amount of light absorbed in the tissue. Three non-pulsatile factors are known to cause these slow variances in the DC component of the plethysmographic wave, namely the Mayer wave, respiration, and, to a smaller extent, temperature changes within the tissue. Generally, variance in temperature in the tissue occurs at such a low frequency that it is easily distinguishable from the effects of respiration and the Mayer wave on the plethysmographic wave. However, the Mayer wave, as will be discussed herein, varies on a frequency similar to that of the respiration, which makes it difficult to isolate variances in the raw plethysmographic signal caused solely by the Mayer wave or solely by respiration.

The Mayer Wave:

The Mayer wave is generally considered to be an isolation of the pressure reflex control system. It is attributed mainly to the baroreceptor reflex (i.e., a neural receptor as in the arterial walls, sensitive to changes in pressure) and is associated with the autonomic nervous system (i.e., the vasomotor center). The Mayer wave in general causes variations in arterial blood pressure, heart rate and/or vasoconstriction which cause a variation in the blood volume of the patient's tissue. This variation in the tissue is seen in the plethysmographic signal as a change in the DC value due to increased/decreased light absorption by the varying tissue volume. The cycle of the Mayer wave is as follows: the baroreceptors sense an increase in pressure which inhibit the sympathetic nerve system which, in turn, reduces the pressure. This pressure drop causes the baroreceptors to excite the sympathetic system, the blood pressure rises, and the cycle starts over again. The response of the pressure to the reflex is not instantaneous; the period of the Mayer wave is generally held to be between six and twenty seconds in humans, or around 0.05 to 0.15 hertz. The Mayer wave can affect the blood pressure within the arteries and veins by as much as 40 milligrams of mercury (40 mm Hg.) However, the strength of the Mayer wave varies between individuals, generally decreases with age, and increases upon concentration.

Respiration:

Respiration also causes changes in the heart rate, vasoconstriction, arterial blood pressure and/or venous blood pressure, which can also affect the DC component of a plethysmographic wave by increasing or decreasing the amount of tissue the light signals pass through. The generally accepted effect of respiration on arterial pressure is a rise in pressure during the early part of expiration (exhaling), and a falling pressure during the remainder of the respiratory cycle, which can cause blood pressure to rise and fall by as much as 20 milligrams of mercury (20 mm Hg.) Respiration can be expected to occur between 0 and 30 times per minute with a typical adult resting respiration cycle being between 4 and 12 breaths per minute or from 0.07 to 0.2 hertz. The changes caused by respiration in heart rate and vasoconstriction are generally considered to be a spillover from the central nervous center to the vasomotor center which cause the same effects as the Mayer wave. The frequencies of the Mayer wave and respiration may overlap and have similar effects on blood pressure. Therefore, the effects of the Mayer wave and respiration on the volume of blood in the tissue may cancel one another out leaving no indication that they occurred at all in the raw DC waveform. For example if the Mayer wave causes the baroreceptors to inhibit the sympathetic nerve system which, in turn, reduces blood pressure while a patient is expiring which causes an increase in pressure, the effects of the two actions may cancel one another out as far as changes in the volume of tissue are concerned. Therefore it becomes difficult if not impossible from a raw plethysmographic signal the effects caused solely by respiration and the effect caused solely by the Mayer wave.

Though similar in their effects on the body, there are differences between the effects of the Mayer wave and respiration. In respiration, the changes in arterial blood pressure and/or venous blood pressure are caused mainly by thoracic pressure changes. As will be appreciated, thoracic pressure changes are caused by the expansion and contraction of the chest cavity (i.e., thorax) during respiration. Changes in thoracic pressure due to respiration cause accumulation of blood in the vessels inside the chest wall during inspiration (inhaling). The blood pressure change is generally considered to originate from decreased left ventricular filling during inspiration and increased filling during expiration. The venous pressure and thus the venous filling, changes as a direct result of the sucking of blood towards the chest during inspiration and the expulsion of blood from the chest during expiration. This sucking of blood into the chest causes a change in the amount of venous blood in the tissue but does not affect the amount of arterial blood in the tissue. Therefore, respiration causes a variation in the ratio of arterial blood over venous blood in the tissue. In contrast the variation in arterial blood pressure, heart rate and/or vasoconstriction caused by the Mayer wave, has no independent effect on venous blood in relation to arterial blood. In fact, changes in heart rate, blood pressure, and/or vasoconstriction generally affect both the arterial and venous blood in approximately the same way, keeping their relative amounts (i.e., ratio) more or less constant. Therefore, the Mayer wave does not affect the ratio of arterial blood over venous blood in the tissue. Accordingly, by monitoring this ratio for changes over a frequency corresponding with respiration, respiration may be monitored using a pulse oximeter.

The ratio of venous blood to arterial blood is difficult or substantially impossible to measure from the raw plethysmographic signal, therefore, in order to determine this ratio the raw signal must be processed. Assuming the oxygen saturation of the incoming blood and oxygen consumption in the tissue are constant, the ratio of arterial blood over venous blood will be proportional to the oxyhemoglobin over the de-oxyhemoglobin ($HbO_2$/Hb) concentration ratio of the tissue as a whole since, typically, arterial blood is oxygen rich and venous blood is oxygen depleted. Therefore, changes in the arterial blood over venous blood ratio can be monitored by measuring changes in the above ratio. For example, the $HbO_2$/Hb ratio will rise during inspiration and fall during expiration over a cycle frequency between 0 and 1.5 hertz.

Derivation of an Algorithm for Monitoring $HbO_2$/Hb in the Tissue as a Whole:

The microprocessor uses the separated DC component of the measured signals to calculate the ratio of oxygenated versus deoxygenated blood. By using only the DC component of the plethysmographic signal, the oxygenated versus de-oxygenated blood ratio will be calculated for the tissue as a whole. Using the Lambert-Beer law, the absorption of light with a first wavelength $\lambda_1$ and an absorption coefficient $\alpha_1$ is as follows:

$$\left[\log\frac{I}{I_o}\right]_{\lambda_1} = -[\alpha_{1HbO2}(HbO_2) + \alpha_{1Hb}(Hb)]L \qquad (1)$$

solving for the HbO$_2$/Hb ratio:

$$\frac{HbO_2}{Hb} = \frac{-1}{\alpha_{1HbO2}L(Hb)}\left[\log\frac{I}{I_o}\right]_{\lambda 1} - \frac{\alpha_{1Hb}}{\alpha_{1HbO2}} \quad (2)$$

For a second wavelength $\lambda_2$ and an absorption coefficient $\alpha_2$:

$$\frac{HbO_2}{Hb} = \frac{-1}{\alpha_{2HbO2}L(Hb)}\left[\log\frac{I}{I_o}\right]_{\lambda 2} - \frac{\alpha_{2Hb}}{\alpha_{21HbO2}} \quad (3)$$

As will be appreciated, the length will be the same for each equation since both wave lengths of light travel through the same portion of tissue. Rearranging the above equation and solving:

$$\frac{-1}{L(Hb)} = \left\{\frac{HbO_2}{Hb} + \frac{\alpha_{2Hb}}{\alpha_{2HbO2}}\right\} / \left\{\frac{1}{\alpha_{2HbO2}}\left(\log\frac{I}{I_o}\right)_{\lambda 2}\right\} \quad (4)$$

Substituting this value into the equation (2) and reducing:

$$\frac{HbO_2}{Hb} = \frac{\alpha_{2Hb}Q - \alpha_{1Hb}}{\alpha_{1HbO2} - \alpha_{2HbO2}Q} \quad (5)$$

Where $$Q = \log(I/I_o)_{\lambda 1}/\log(I/I_o)_{\lambda 2} \quad (6)$$

Allowing $\lambda_1$ to be red light and $\lambda_2$ to be infrared light, the final result is:

$$\frac{HbO_2}{Hb} = \frac{\alpha_{IRHb}Q - \alpha_{redHb}}{\alpha_{redHbO2} - \alpha_{IRHbO2}Q} \quad (7)$$

where:

$$Q = \log(I/I_o)_{red}/\log(I/I_o)_{IR} \quad (8)$$

Practical Algorithm to Calculate HbO$_2$/Hb in the Tissue as a Whole:

Because $I_o$ is generally unknown, Q is not calculated directly. Rather, to determine the ratio of oxyhemoglobin to de-oxyhemoglobin the ratio is expressed in terms which may be measured. A method used in arterial blood saturation (i.e., the AC component) calculations to solve this problem is differential absorption. In differential absorption calculations, another representation of Beer' law is used:

$$I = I_o \exp(-\epsilon d)tm \quad (9)$$

where $\epsilon$ is the extinction coefficient (i.e., color) of the blood and d is the volume of arterial blood. Again we have $I_o$, which is unknown, however by taking the derivative of the above equation the change in intensity over the measured intensity can be determined:

$$\frac{\Delta I}{I} \approx -\epsilon \cdot \Delta d \quad (10)$$

As the change in the amount of arterial blood ($\Delta d$) is the same for both wavelengths it will cancel out in subsequent calculations and need never be directly measured. However, since the DC component is used $\Delta d$ is not the change in arterial blood due to pulse, but the slow change in the tissue volume due to respiration and the Mayer wave.

The Ratio of Ratios is a variable used in calculating blood oxygen saturation levels in the blood of a patient and may be calculated using instantaneous differential values or peak-to-trough measurements of the red and infrared waveforms. Instantaneous differential values are determined in relation to two or more proximate samples for each channel. Peak-to-trough measurements are obtained by taking the natural logarithm of the ratio of the peak value of the red plethysmographic signal divided by the valley measurement of the red plethysmographic signal. The aforementioned value is then divided by the natural logarithm of the ratio of the peak value of the infrared plethysmographic signal divided by the value of the valley measurement of the infrared plethysmographic signal, or vice versa. In either case, the signals may be measured several times over a given time period and averaged or regression analysis may be performed to obtain the desired ratio of ratios. However, when using differential absorption, the same Ratio of Ratios may be expressed as:

$$R = \left(\frac{\Delta I}{I}\right)_{\lambda 1} / \left(\frac{\Delta I}{I}\right)_{\lambda 2} \quad (11)$$

Therefore, R can be derived by taking the derivative of the Beer Lambert Function without the use of logarithms. Plugging in the differential absorption as $\Delta I/I = \epsilon \Delta d$ for each wavelength (change in volume ($\Delta d$) is the same for both wavelengths and therefore cancels) and assuming HbO$_2$+Hb=1, leads to:

$$R = \frac{\varepsilon_1}{\varepsilon_2} = \frac{\varepsilon_{1HbO2}(HbO_2) + \varepsilon_{1Hb}(Hb)}{\varepsilon_{2HbO2}(HbO_2) + \varepsilon_{2Hb}(Hb)} \quad (12)$$

Rearranging and solving the equation:

$$\frac{HbO_2}{Hb} = \frac{\varepsilon_{1Hb} - R\varepsilon_{2Hb}}{R\varepsilon_{2HbO2} - \varepsilon_{1HbO2}} \quad (13)$$

As will be appreciated, all the variables in equation (13) may be determined by processing the plethysmographic signals that pass through the tissue in any of several ways known to those skilled in the art. For example, the extinction coefficients may be determined (using logarithms or derivatives) to solve equation (9) for each wavelength as taught by Mortz U.S. Pat. No. 5,934,277. Alternatively, the processor may store look-up tables that contain extinction curves for RHb and HbO$_2$ versus the center wavelengths of the light emitted through the patient's tissue as taught by Jarman U.S. Pat. No. 5,842,979. The Ratio of Ratios may be calculated using the natural logarithmic method described above using the peaks and valleys of the DC components of the plethysmographic signals. By monitoring the resulting value of equation (13) over a predetermined time period (i.e., frequency) for cyclical variations, it is possible to monitor respiration using plethysmographic signals. For example, the resulting value may be plotted versus time such that a respiratory wave may be produced.

Figure 4:
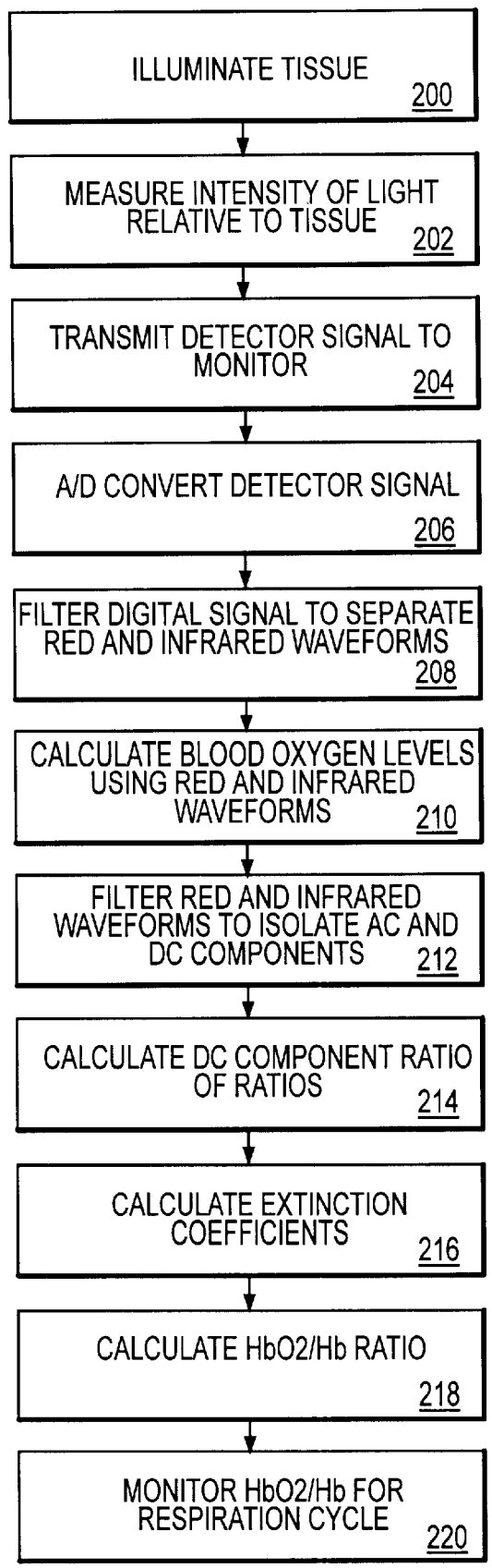
FIG. 4 is a flow chart illustrating a method in accordance with the present invention.

Referring to FIG. 4, a method of monitoring respiration with a pulse oximeter according to the present invention is set forth. As described above, the first step is to illuminate (200) the tissue of the subject with a plurality of light signals emitted at different corresponding centered wavelengths. In order to determine the volume and/or the color of the blood in the tissue at least two light sources having different centered wavelengths are utilized. Preferably a first light source will have a first wavelength in infrared range and a second light source will have a second wavelength in the red range. The intensity of the light transmitted through or reflected from the tissue under test is measured (202) through the use one or more photodetectors which produces a signal corresponding to the intensity of the light it receives. This signal may comprise a single multiplexed signal which represents the intensity of both the first and second wavelengths of light transmitted relative to the tissue or separate signals for each wavelength. This intensity measurement (i.e., detector signal), represented in an analog form, is transmitted (204) to the plethysmographic monitor. Once received by the monitor, the analog signal is converted (206) into a digital equivalent using an analog to digital (A/D) converter, which may be part of the probe interface with the monitor. The resulting digital signal(s) is stored by the monitor and manipulated by the processor according to instructions stored therein. In particular, the digital signal is filtered (208) such that the infrared and red waveforms are separated from one another so they may be individually monitored. Once the red and infrared waveforms are separated from one another, the Blood Oxygen Saturation Level of the tissue may be calculated (210) by calculating the Ratio of Ratios from the peaks and valleys of the red and infrared waveforms as known in the art. More preferably, the Ratio of Ratios may be calculated based on instantaneous differential values and multiple values may be analyzed in a regression analysis to obtain a result related to blood oxygenation. The red and infrared waveforms are further filtered (212) to separate the AC and DC components contained therein. Once the DC component of both the red and infrared waveforms is available, the processor may begin taking samples over predetermined time period from these waveforms. From these sample or data points, the processor is able to calculate (214) the DC component Ratio of Ratios by taking an average of the peak and valley values of the red and infrared DC waveforms or other differential values over a predetermined time period and performing logarithmic computations with these values. In addition, the processor is configured to calculate (216) the extinction coefficients for both the red and infrared waveforms for the $HbO_2$ and the RHb. Once a DC component Ratio of Ratios and extinction coefficients are calculated, the processor calculates (218) the $HbO_2/Hb$ ratio and produces an output indicative thereof. For example, the monitor may plot this ratio versus time such that a respiration wave is produced. The respiration wave in this instance will comprise a cyclical waveform increasing and decreasing with the respiration cycle. Accordingly each peak to peak or valley to valley measurement would correspond with a full respiratory cycle that may be easily monitored (220) along with blood oxygen saturation levels typically taken by the pulse oximeter. It will be appreciated that other waveform related analysis may be utilized to obtain respiration information.

While various embodiments of the present invention and then described in detail, is apparent to further modifications and adaptations of the invention will occur to those skilled in the art. However, it is to be expressly understood that such modifications and adaptations are within spirit in scope of the present invention.

What is claimed:

1. A method for monitoring a patient's respiration through changes in the patient's blood concentrations, said method comprising the steps of:
    monitoring a portion of perfused tissue to obtain at least one plethysmographic signal;
    processing said at least one plethysmographic signal to obtain pulsatile AC signal component information and substantially non-pulsatile DC signal component information, wherein said non-pulsatile DC signal component information reflects a variability separate from a pulse of a patient;
    determining a relative concentration of arterial blood and venous blood in said tissue based on said DC signal component information; and
    monitoring said relative concentration of arterial and venous blood based on said DC signal component information over time to determine a respiration frequency from increases and decreases in said relative concentration.

2. The method of claim 1, wherein said step of monitoring said relative concentration of venous and arterial blood is performed non-invasively.

3. The method of claim 2, wherein said step of non-invasively monitoring is performed photoplethysmographically.

4. The method of claim 3, wherein said step of photoplethysmographically monitoring further comprises the steps of:
    applying electromagnetic radiation of at least two wavelengths to said portion of tissue;
    detecting signals for each said wavelength applied to said portion of tissue; and
    obtaining said substantially non-pulsatile DC signal component information for each of said at least two wavelengths.

5. The method of claim 1, wherein said step of determining a relative concentration further comprises:
    determining a first quantitative value associated with arterial blood in said tissue; and
    determining a second quantitative value associated with venous blood in said tissue.

6. The method of claim 5, wherein said first quantitative value is associated with oxygenated hemoglobin ($HbO_2$) and said second quantitative value is associated with de-oxygenated hemoglobin (Hb).

7. The method of claim, 6 wherein said relative concentration is a ratio $HbO_2/Hb$ of said oxygenated hemoglobin and said de-oxygenated hemoglobin.

8. The method of claim 7 wherein said ratio is calculated using the following:

$$\frac{HbO_2}{Hb} = \frac{\varepsilon_{1Hb} - R\varepsilon_{2Hb}}{R\varepsilon_{2HbO2} - \varepsilon_{1HbO2}}$$

wherein, $\varepsilon_{1Hb}$ and $\varepsilon_{2Hb}$ represent extinction coefficients of said de-oxygenated hemoglobin for a first and second wavelengths of said signal plethysmographic, respectively, and $\varepsilon_{1HbO2}$ and $\varepsilon_{2HbO2}$ represent extinction coefficients of said oxygenated hemoglobin for said first and second wavelengths of said plethysmographic signal, respectively, and R represent the ratio of ration for said plethysmographic signal.

9. The method of claim 1, wherein said relative concentration is monitored for said variations over a frequency range of 0 to 1.5 hertz.

10. An apparatus for monitoring respiration, using optical signals to identify changes in values related to blood oxygen levels caused by said respiration, said apparatus comprising:
    at least a first emitter for controllably emitting at least first and second wavelengths of electromagnetic radiation to a portion of living tissue;
    a detector for detecting signals relative to said emitted first and second wavelengths of said electromagnetic radiation and producing a detector signal indicative thereof; and a processor operable to receive said detector signal, said processor further operable for:

processing said detector signal to obtain pulsatile AC signal component information and substantially invariant DC signal component information; and using said DC signal component information to determine a quantitative value related to a ratio of arterial blood to venous blood of said tissue, wherein said non-pulsatile DC signal component information reflects a variability separate from a pulse of a patient;

monitoring said value to determine variations in said ratio over a predetermined frequency range indicative of respiration; and generating an output signal indicative of respiration.

11. The apparatus of claim 10, wherein said at least a first emitter comprises at least a first light emitting diode.

12. The apparatus of claim 11, further comprising a first and second light emitting diode for emitting electromagnetic radiation in the visible and infrared range respectively.

13. The apparatus of claim 10, wherein said processor monitors said value over a predetermined time cycle for changes in said value indicative of respiration.

14. The apparatus of claim 13, wherein said predetermined time cycle is from 0 to 1.5 hz.

15. The apparatus of claim 10, wherein said quantitative value includes a first value associated with oxygenated hemoglobin (HbO$_2$) and a second value associated with de-oxygenated hemoglobin (Hb).

16. The apparatus of claim 10, wherein said ratio is calculated using the following:

$$\frac{HbO_2}{Hb} = \frac{\varepsilon_{1Hb} - R\varepsilon_{2Hb}}{R\varepsilon_{2HbO2} - \varepsilon_{1HbO2}}$$

wherein, $\varepsilon_{1Hb}$ and $\varepsilon_{2Hb}$ represent extinction coefficients of said de-oxygenated hemoglobin for a first and second wavelengths of said plethysmographic signal, respectively, and $\varepsilon_{1HbO2}$ and $\varepsilon_{2HbO2}$ represent extinction coefficients of said oxygenated hemoglobin for said first and second wavelengths of said plethysmographic signal, respectively, and R represent the ratio of ration for said plethysmographic signal.

17. A method for monitoring a patient's respiration through changes in the patient's blood concentrations, said method comprising the steps of:

applying first and second optical signals to a portion of tissue, wherein said first and second optical signals have different wavelengths;

detecting said first and second optical signals as modulated by said tissue and generating a detector signal representative of said first and second optical signals;

processing said detector signal to obtain first and second DC signal components corresponding with said first and second optical signals;

determining a relative concentration of arterial and venous blood in said tissue based on said first and second DC signal components; and monitoring said relative concentration to identify a variation associated with respiration.

18. The method of claim 17, wherein monitoring comprises monitoring said relative concentration over a predetermined time cycle to identify said variation.

19. The apparatus of claim 18, wherein said predetermined time cycle is from 0 to 1.5 hz.

20. The method of claim 17, wherein said step of determining a relative concentration further comprises:

determining a first quantitative value associated with arterial blood in said tissue; and determining a second quantitative value associated with venous blood in said tissue.

21. The method of claim 20, wherein said first quantitative value is associated with oxygenated hemoglobin (HbO$_2$) and said second quantitative value is associated with de-oxygenated hemoglobin (Hb).

22. The method of claim, 7 wherein said relative concentration is a ratio, HbO$_2$/Hb, of said of oxygenated hemoglobin and said de-oxygenated hemoglobin.

* * * * *